United States Patent [19]

Horng et al.

[11] Patent Number: 5,322,436
[45] Date of Patent: Jun. 21, 1994

[54] ENGRAVED ORTHODONTIC BAND

[75] Inventors: Bryan L. Horng, Rowland Heights; Steven A. Martin, Lafayette, both of Calif.

[73] Assignee: Minnesota Mining and Manufacturing Company, St. Paul, Minn.

[21] Appl. No.: 968,008

[22] Filed: Oct. 26, 1992

[51] Int. Cl.$^5$ .............................................. A61C 3/00
[52] U.S. Cl. ...................................................... 433/23
[58] Field of Search ............................. 433/23, 229, 8

[56] References Cited

U.S. PATENT DOCUMENTS

| | | | |
|---|---|---|---|
| 436,972 | 9/1890 | Engel | 433/23 X |
| 2,759,265 | 8/1956 | Johnson | 32/14 |
| 3,817,588 | 6/1974 | Helmers | 433/77 X |
| 3,931,458 | 1/1976 | Dini | 358/297 |
| 4,120,090 | 10/1978 | Kesling | 433/23 |
| 4,195,046 | 3/1980 | Kesling | 433/6 X |
| 4,304,981 | 12/1981 | Gappa | 219/121 LF |
| 4,439,154 | 3/1984 | Mayclin | 433/229 |
| 4,616,209 | 10/1986 | Mahon | 340/309.15 |
| 4,626,209 | 12/1986 | Tsai et al. | 433/9 |
| 4,693,567 | 9/1987 | Ozaki | 350/433 |
| 4,842,513 | 6/1989 | Haarmann | 433/9 |
| 4,900,252 | 2/1990 | Liefke et al. | 433/27 |
| 5,044,955 | 9/1991 | Jagmin | 433/229 |
| 5,052,928 | 10/1991 | Andersson | 433/172 |
| 5,094,619 | 3/1992 | McLaughlin | 433/203.1 |

FOREIGN PATENT DOCUMENTS

| | | |
|---|---|---|
| 0085484 | 8/1983 | European Pat. Off. . |
| 0327628 | 1/1992 | European Pat. Off. . |
| 2724779 | 12/1978 | Fed. Rep. of Germany . |
| 2-82966 | 3/1990 | Japan . |
| 89/01318 | 2/1989 | World Int. Prop. O. . |

OTHER PUBLICATIONS

Rocky Mountain Orthodontic Catalog, Jan. 1959 p. 38.
Dentaurum Advertisement in British Journal of Orthodontics, vol. 19, No. 3, Aug. 1992.
Dentaurum Laser I.D. System Advertisement, undated.
Mark Takarabe, "Precision Sensing With Lasers", *Machine Design*, Jul. 23, 1992, pp. 62, 64, 66.

*Primary Examiner*—Gene Mancene
*Assistant Examiner*—Nicholas D. Lucchesi
*Attorney, Agent, or Firm*—Gary L. Griswold; Walter N. Kirn; James D. Christoff

[57] ABSTRACT

An orthodontic band has a laser engraved mark with a white, frosty appearance. The mark is characterized by an absence of dark surface oxides, and is aesthetic and easy to read.

5 Claims, 1 Drawing Sheet

ENGRAVED ORTHODONTIC BAND

BACKGROUND OF THE INVENTION

1. Field of the Invention

This invention relates to an orthodontic band having an engraved identification mark.

2. Description of the Related Art

Orthodontic treatment involves movement of the teeth to desired positions. During treatment, small slotted bodies known as brackets are typically bonded to anterior teeth, and an arch wire held in the slots functions as a track to guide movement of the teeth. The teeth are commonly moved by bends or twists placed in the arch wire or by elastic members connected between the brackets of certain teeth.

Ends of the arch wires are normally anchored in devices known as buccal tubes that are mounted on molar teeth. Occasionally, buccal tubes are bonded directly to an exterior surface of the molar teeth using a small amount of adhesive in a manner similar to the method of bonding brackets directly to anterior teeth. However, buccal tubes are often subjected to relatively large forces from occluding teeth as well as forces exerted by the arch wire, and as a result may spontaneously debond from the tooth. Rebonding of the buccal tube can be achieved, but is a nuisance both to the orthodontist and the patient.

As a consequence, buccal tubes are commonly welded to metallic orthodontic bands that are placed around the molar teeth to provide a stable base for mounting the buccal tubes. Orthodontic bands are made in a variety of shapes and sizes, so that a band with the proper contour and circumferential dimensions can be selected in each instance to tightly fit onto the molar tooth. Bands are also available for use with anterior, cuspid and bicuspid teeth in instances where a relatively strong connection to such teeth is desired.

Orthodontic bands are often provided with an inked identification mark that includes indicia describing which tooth the band is intended to fit, as well as a notation signifying the manufacturer's designated size of the band. Band selection is often made by the orthodontist by first visually estimating the size of the chosen tooth and then selecting a few bands of different sizes that appear to be close in size to the tooth. The bands selected by the orthodontist are placed on a setup tray that is located by the patient.

Next, the bands on the tray are placed on the chosen tooth for a trial fitting until the band having the best fit is found. The remaining bands are sterilized to reduce the risk of cross-contamination before being returned to a storage container. Normally, the storage container is partitioned to separate an inventory of bands by tooth type and size.

Sterilization procedures vary among orthodontists, and typical procedures may use an autoclave, chemical clave, dry heat or a cold sterilizing solution such as that sold under the trademark "CIDEX 7". Unfortunately, sterilization procedures may adversely affect the inked identification mark and make the mark difficult to read, especially if the band is sterilized a number of times. Once the mark is illegible, it is often difficult to find the proper partitioned location in the storage container for the band, as there may be over one hundred fifty storage locations in one or containers for the various band sizes.

Orthodontic bands having a dark laser engraved identification mark that appears brown in color have been sold in the past. However, laser engraved marks that are brown in color are not entirely satisfactory, as it is sometimes observed that a brown mark is more difficult to see after repeated chemical sterilizations. Moreover, many orthodontic patients are concerned about the appearance of appliances that are placed in their mouth, and may not be entirely pleased with a brown identification mark on the surface of a bright, shiny stainless steel band.

SUMMARY OF THE INVENTION

The present invention is directed toward an orthodontic band having an engraved identification mark that is substantially white in color. The white mark is highly aesthetic especially against the color of a stainless steel background and yet is relatively easy to perceive.

It has been found that the brown color of known laser engraved marks of orthodontic bands is due to the presence of dark oxides on the surface of the engraved mark that absorb light and cause the mark to appear as a brown color. In contrast, the identification mark of the present invention is relatively free of dark surface oxides and perception of the mark is due primarily to the phenomenon of light scattering. Preferably, the mark of the invention is relatively wide and has a roughened topography that enables the white mark to present a pleasing frosty appearance. The absence of dark surface oxides enables the practitioner to readily observe whether or not corrosion is present as may occasionally occur with some bands after repeated sterilizations, since it is generally deemed undesirable to use a corroded appliance in the mouth.

DETAILED DESCRIPTION OF THE PREFERRED EMBODIMENT

Figure 1:
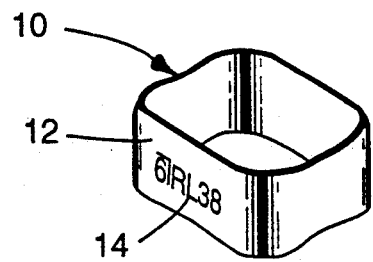
FIG. 1 is a perspective view of an orthodontic band made in accordance with the present invention.
Figure 2:
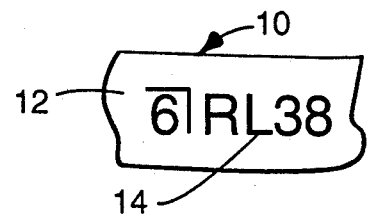
FIG. 2 is an enlarged, fragmentary elevational view of a portion of the band shown in FIG. 1, and particularly showing a white identification mark engraved on an outer surface of the band.

An orthodontic band 10 according to the invention is shown in FIGS. 1 and 2 and is made of a metallic material, preferably stainless steel type 305. The band 10 has a height, contour and inner circumference that closely matches the expected shape of particular teeth without interference with the gingiva.

The band 10 includes an outer wall 12 that has an engraved identification mark 14 preferably made by a laser. The mark 14 includes numerals sufficient to identify the location of the tooth for which the band 10 is intended, as well as a manufacturer's notation that represents a size of the band 10. The mark 14 is preferably located on a portion of the wall 12 that is positioned in an interproximal manner on a mesial side of the tooth when the band 10 is placed over the tooth in its correct orientation.

The mark 14 is preferably made using laser marking apparatus operated in a "wobble" mode wherein the beam of the laser revolves along a small diameter circular path as the beam is also advanced along a straight line, so that a spiral pattern is established. Preferably, the beam while operating in the wobble mode makes multiple passes along parallel lines that are spaced slightly apart from each other, so that the beam has passed over the surface of the intended mark a number of times and a relatively wide mark is made.

The band 10 after engraved with the mark 14 is cleaned with an alkaline solution, rinsed and dried. Next, the band 10 is passivated using an acidic solution, and then again rinsed and dried. The resultant cleaned and passivated mark 14 appears as a rough but shiny surface in contrast to the smooth and shiny surface of adjacent regions of the band 10 that are not engraved by the laser, such that the mark 14 has a white, frosty appearance.

Preferably, variables of the laser engraving apparatus such as beam speed, current and pulse frequency are selected to make a mark that is relatively wide and deep, yet does not heat the wall 12 to such a degree that undue discoloration in the form of brown or black surface oxides are observed. However, small amounts of dark surface oxides established during the laser engraving are normally not a cause for concern, as such small amounts are procedures. The resulting mark 14 is pleasing in appearance and easy to read after repeated sterilizations. The mark 14 does not change in appearance after repeated sterilizations as might occur with a dark laser engraved mark that is perceived in substantial part by the presence of dark surface oxides.

The average concentration of oxides in an external surface layer of the mark 14 is preferably not substantially greater than the average concentration of oxides in a similar layer of the wall 12 next to the mark 14, in contrast to conventional laser engraved bands having a mark with a significantly higher amount of oxides in a surface layer of the identification mark in comparison to regions next to the mark. The relative absence of oxides enables the absorption of light to be substantially avoided. The average concentration of surface oxides is measured by photoelectron spectroscopy, using a focused x-ray beam and sputter-etching the surface with an argon beam to obtain atomic percent concentrations of iron and oxide within the outer 3000 angstroms of the surface.

Figure 3:
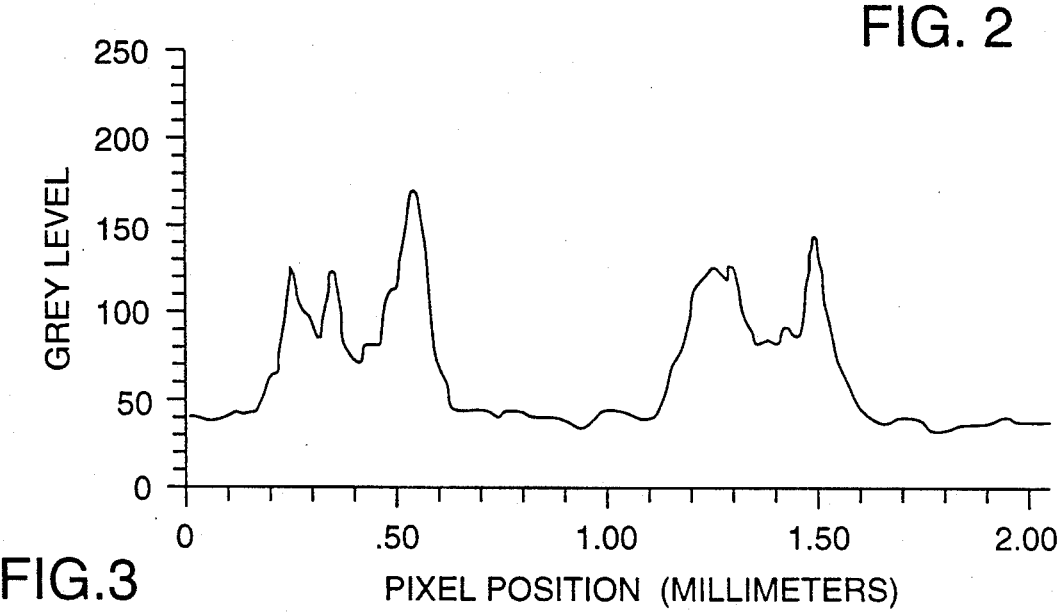
FIG. 3 is a graph of reflectance measurements for a selected area of a band made according to the present invention, wherein the measurements were taken along regions that were laser engraved and adjacent, unengraved regions.
Figure 4:
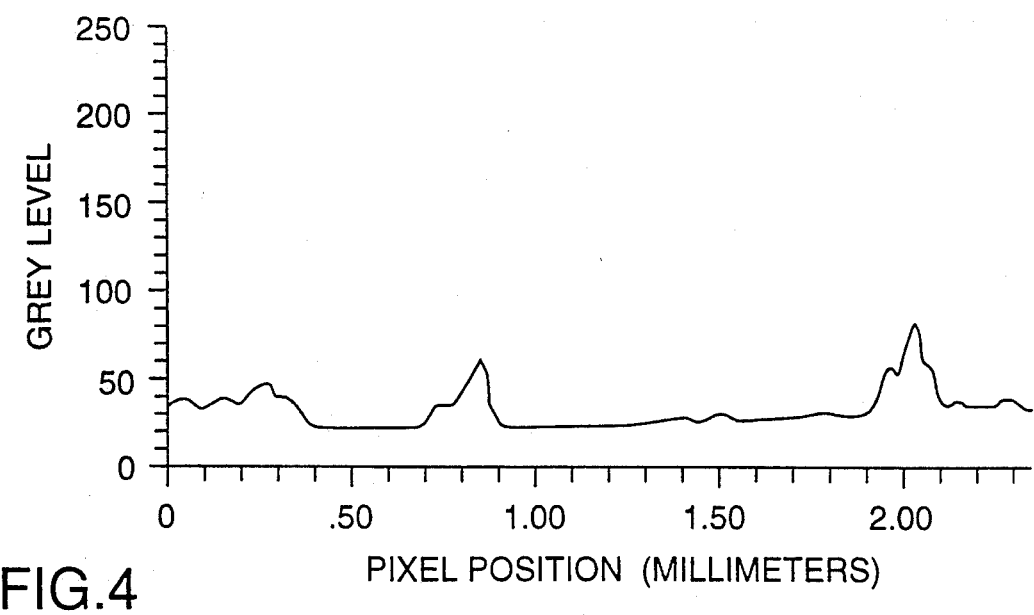
FIG. 4 is a graph of reflectance measurements of a selected area of a prior art orthodontic band taken across a dark, laser engraved identification mark as well as adjacent, unengraved regions.

FIGS. 3 and 4 are graphs of reflectance measurements made using a Leica Q-570 Image Analyzer with a 1X objective configured for dark field illumination. A diffuse reflectance standard comprising a white ruler with black markings was used to adjust illumination intensity such that the white regions (corresponding to 100% diffuse reflectance) provided a measured value of 255, and the black regions (corresponding to 0% diffuse reflectance) provided a measured value of 0. In FIGS. 3 and 4, the reflectance values were obtained by averaging line scans over a rectangular area that included portions of the indicia as well as portions of adjacent, unengraved areas of the exterior wall of the bands.

FIG. 3 is a graph of a reflectance measurement profile of a portion of an exterior wall of a band according to the present invention. Unengraved regions of the band provided an average "baseline" gray level measurement of about 30-40 in FIG. 3, while measurements across the laser identification marks produced much higher values ranging from about 70 to 170. FIG. 4 is a graph of a similar reflectance measurement profile made of a prior art brown laser marked band, wherein baseline values for unengraved regions of the band ranged from about 20 to about 35, and measurements for three laser marked regions of the band ranged from about 30 to about 80.

The white, frosty laser marked band of the present invention provides a higher ratio of peak reflectance to background reflectance than known bands having a brown laser engraved mark. The peak to background reflectance ratio corresponds to the relative amount of light scattered by the identification mark and is indicative of the contrast between the mark and adjacent background or unengraved regions. Consequently, even though the mark of the present invention is light in color and not dark, it is relatively easy to discern.

EXAMPLE

An orthodontic band was selected that was similar to an orthodontic band for an lower left first tooth except that the band was not chemically cleaned and passivated as is carried out with conventional bands commercially available from 3M Unitek. The band was placed over a tapered mandrel and held in a fixed position with a working clearance of approximately 19 cm from the focusing lens of a YAG laser engraving system ("EMBLEM", Control Laser Corporation). The laser engraving apparatus was set to provide a beam speed of 5.1 cm/seconds, a character height of 0.15 cm, a QSMODE of 1 khz, a current of 11 amps, and a character line width of 0.01 cm. The resulting identification mark had a slight discoloration.

Next, the band was immersed for five minutes in an alkaline solution at about 80° C. made by dissolving 1.6 kg of alkaline metal cleaner ("DIVERCLEAN HP", Diversey Wyendotte Corporation) in 38 l of tap water. The band was then rinsed in tap water for five minutes. Next, the band was immersed for 40 minutes in a descaling solution at about 80° C. made by dissolving 5 kg of alkaline metal descaler ("DIVERSCALE" 299, Diversey Wyendotte Corporation) in 38 l of tap water. The band was then rinsed in tap water for 10 to 15 minutes. Next, the band was neutralized at room temperature for one minute in an acidic solution made by mixing an equal amount of "EVERITE" 2 (Diversey Chemicals) with an equal amount of tap water. The band was then rinsed in tap water for 5 minutes.

The cleaned band was then passivated at about 50° C. for 40 minutes in a 22% nitric acid solution. Subsequently, the band was rinsed in tap water for 10 minutes, rinsed in deionized water for 10 minutes, and dried in a spin dryer (New Holland, model K11) for 2 minutes.

The resulting laser engraved identification mark lost its originally slight discoloration and had a white, frosty appearance that was aesthetically pleasing.

We claim:

1. An orthodontic band having a laser engraved identification mark that is sufficiently free of dark surface oxides such that said identification mark is substantially white in color, said identification mark having a rougher surface than adjacent surfaces of the band, thereby presenting a frosty appearance.

2. The band of claim 1, wherein said band includes a wall and said mark is on said wall, and wherein said mark has an average concentration of oxides in an external surface layer that is not substantially greater than the average concentration of oxides in a similar layer of said wall next to said mark.

3. The band of claim 1, wherein said identification mark is a spiral pattern laser engraved mark.

4. The band of claim 3, wherein said spiral pattern comprises multiple spirals that extend along side-by-side, generally parallel paths.

5. An orthodontic band having a wall with a laser engraved identification mark, said mark having an average concentration of oxides in an external surface layer that is not substantially greater than the average concentration of oxides in a similar layer of said wall next to said mark, said mark being sufficiently free of dark surface oxides to present a substantially white appearance.

* * * * *